United States Patent
Bonakdar Sakhi

(10) Patent No.: US 11,042,778 B2
(45) Date of Patent: Jun. 22, 2021

(54) GENERATING REALISTIC ORGAN X-RAY ANGIOGRAPHY (XA) IMAGES FOR DEEP LEARNING CONSUMPTION

(71) Applicant: INTERNATIONAL BUSINESS MACHINES CORPORATION, Armonk, NY (US)

(72) Inventor: Omid Bonakdar Sakhi, North York (CA)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 163 days.

(21) Appl. No.: 16/205,030

(22) Filed: Nov. 29, 2018

(65) Prior Publication Data
US 2020/0175328 A1 Jun. 4, 2020

(51) Int. Cl.
*G06K 9/62* (2006.01)
*G06N 3/08* (2006.01)
*G06N 3/04* (2006.01)
*G16H 30/20* (2018.01)
*G06T 7/00* (2017.01)

(52) U.S. Cl.
CPC ......... *G06K 9/6255* (2013.01); *G06K 9/6256* (2013.01); *G06N 3/04* (2013.01);
(Continued)

(58) Field of Classification Search
CPC .... G06K 9/6255; G06K 9/6256; G06N 3/088; G06N 3/04; G16H 30/20; G06T 7/0014; G06T 2207/20081; G06T 2207/10116; G06T 2207/30048; G06T 15/00; G06T 7/70; G06T 2207/30244; G06T 2207/20084; G06T 2207/30101
See application file for complete search history.

(56) References Cited

U.S. PATENT DOCUMENTS 9,750,474 B2  9/2017  Sato et al.
2010/0296623 A1  11/2010  Mielekamp et al.
(Continued)

FOREIGN PATENT DOCUMENTS

CN  102715906 B  5/2015
WO  2008047270 A1  4/2008

OTHER PUBLICATIONS

Kang et al., "Cycle Consistent Adversarial Denoising Network for Multiphase Coronary CT Angiography," arXiv Computer Science, Jun. 26, 2018, p. 1-9, arXiv:1806.09748v1.
(Continued)

*Primary Examiner* — Christopher Wait
(74) *Attorney, Agent, or Firm* — David Spalding

(57) ABSTRACT

A method, computer system, and a computer program product for generating one or more realistic x-ray angiography (XA) images for deep learning is provided. The present invention may include generating at least one three-dimensional (3D) model associated with a subject. The present invention may then include projecting the generated 3D model associated with the subject into one or more two-dimensional (2D) images associated with the subject. The present invention may also include creating the one or more realistic XA images of the subject from the one or more 2D images associated with the subject by utilizing a trained deep convolutional neural network.

18 Claims, 6 Drawing Sheets

(52) U.S. Cl.
CPC ........... *G06N 3/088* (2013.01); *G06T 7/0014* (2013.01); *G16H 30/20* (2018.01); *G06T 2207/10116* (2013.01); *G06T 2207/20081* (2013.01); *G06T 2207/30048* (2013.01)

(56) References Cited

U.S. PATENT DOCUMENTS

| | | | |
|---|---|---|---|
| 2012/0189185 A1* | 7/2012 | Chen | G06T 7/149 382/131 |
| 2014/0129200 A1* | 5/2014 | Bronstein | G16H 50/50 703/11 |
| 2018/0374245 A1* | 12/2018 | Xu | A61B 6/5282 |
| 2019/0333219 A1* | 10/2019 | Xu | G06N 3/088 |

OTHER PUBLICATIONS

Mell et al., "The NIST Definition of Cloud Computing," National Institute of Standards and Technology, Sep. 2011, p. 1-3, Special Publication 800-145.

Montoya et al., "3D Deep Learning Angiography (3D-DLA) from C-arm Conebeam CT," American Journal of Neuroradiology, Mar. 22, 2018, p. 1-7, American Society of Neuroradiology.

RSIP, "3D Reconstruction of the Heart," RSIP Vision, p. 1-3, https://www.rsipvision.com/3d-reconstruction-of-the-heart/, Accessed on Nov. 29, 2018.

Zhu et al., "Unpaired Image-to-Image Translation Using Cycle-Consistent Adversarial Networks," IEEE International Conference on Computer Vision (ICCV), 2017, p. 2242-2251, IEEE Computer Society.

\* cited by examiner

GENERATING REALISTIC ORGAN X-RAY ANGIOGRAPHY (XA) IMAGES FOR DEEP LEARNING CONSUMPTION

BACKGROUND

The present invention relates generally to the field of computing, and more particularly to medical image computing.

With the proliferation of deep learning models, more and more people are applying these deep learning models in the domain of medical images. In general, the deep learning models require a large number of images in the training dataset to capture all variations in the data. An example of one of these models is the automatic view recognition of x-ray angiography (XA) images. Medical images, specifically cardiac XA images, are one of most the challenging type of images to gather a dataset of for the purpose of training deep learning models since cardiac XA images capture a large number of variations.

SUMMARY

Embodiments of the present invention disclose a method, computer system, and a computer program product for generating one or more realistic x-ray angiography (XA) images for deep learning. The present invention may include generating at least one three-dimensional (3D) model associated with a subject. The present invention may then include projecting the generated 3D model associated with the subject into one or more two-dimensional (2D) images associated with the subject. The present invention may also include creating the one or more realistic XA images of the subject from the one or more 2D images associated with the subject by utilizing a trained deep convolutional neural network.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
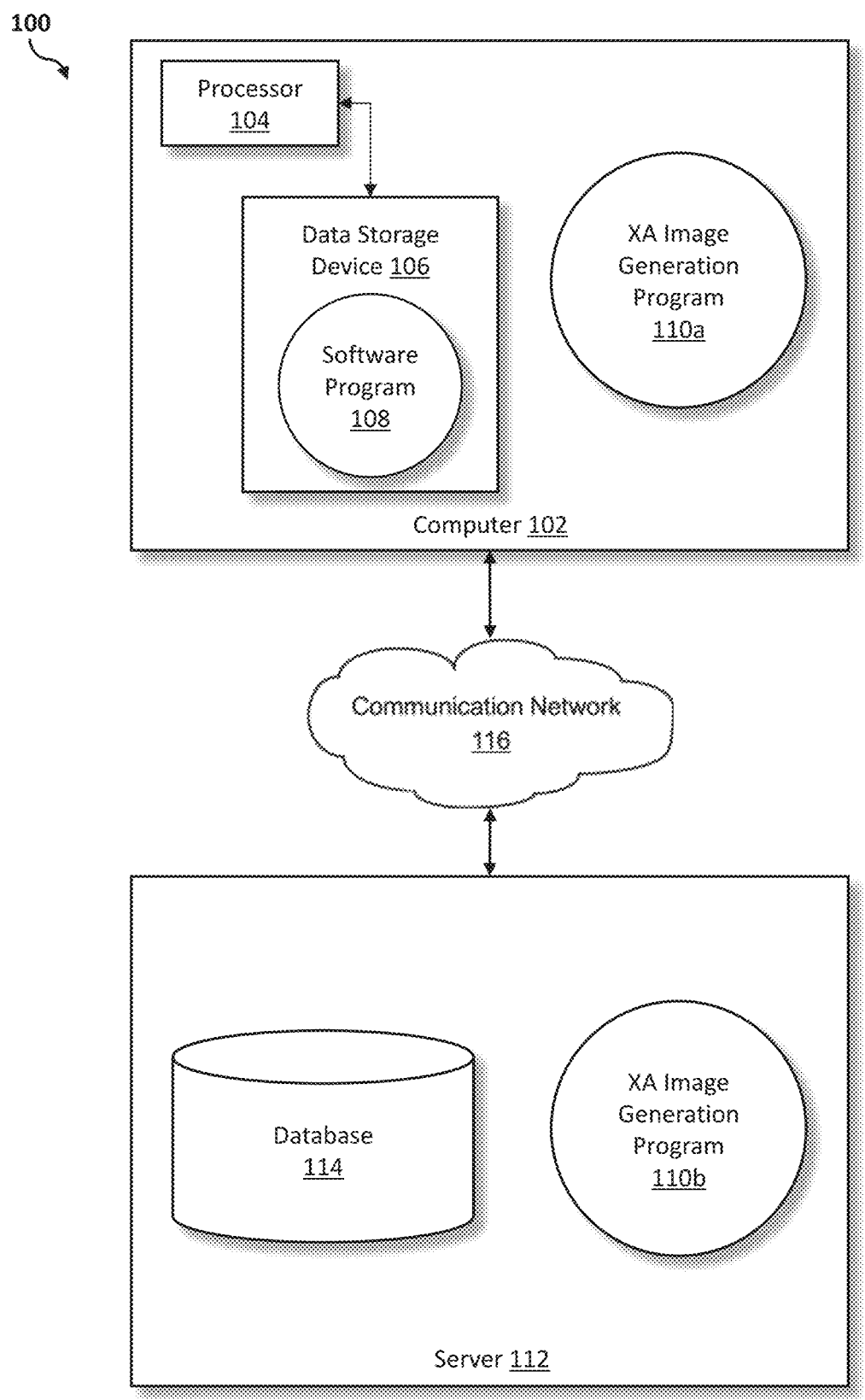
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, Python programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for generating at least one XA image for deep learning consumption. As such, the present embodiment has the capacity to improve the technical field of medical image computing by generating realistic XA images from a simulated model. More specifically, the XA image generation program may generate at least one 3D model of the subject and then the XA image generation program may simulate variations of the subject. The XA image generation program may project the 3D model to a 2D image, and then the XA image generation program may then create a realistic XA image by translating the simulated 2D image.

As previously described, with the proliferation of deep learning models, more and more people are applying these deep learning models in the domain of medical images. In general, the deep learning models require a high number of images in the training dataset to capture all the variations in the data. An example of one of these models is the automatic view recognition of x-ray angiography (XA) images. Medical images, specifically cardiac XA images, are one of most the challenging type of images to gather a dataset of for the purpose of training deep learning models since cardiac XA images capture a large number of variations.

Such variations may include, for example, XA images that are acquired through the angiography procedure which are very noisy, the location of the coronary arteries with respect to the camera may shift or scale due to the beating of the heart or breathing of the patient, the cardiologist may inject, via physical injection of fluid, contrast into the left coronary artery, right coronary artery, or both, the location of the capturing device may change based on the primary or secondary angle, or the disease profile of the patient may greatly influence the location or disappearance of the coronary arteries. Additionally, even if cost is not an issue for acquiring the image data from a partnering hospital or clinic, there may still be difficulty gathering a dataset for the purpose of training deep learning models to capture all of the possible variations.

Therefore, it may be advantageous to, among other things, generate at least one XA image from a simulated model, which uses a medium size dataset of the acquired XA image. Additionally, the XA image generation program may not only have full control over the two angles of the camera, the XA image generation program may also generate a large number of images for the purpose of training discriminative deep learning models with minimal real data which may be utilized to train the Cycle GAN model, thereby saving the cost of acquiring data and minimalizing a person's exposure to radiation (e.g., x-rays). The XA image generation program may be utilized to train prospective medical students.

According to at least one embodiment, the XA image generation program may be utilized to create a dataset for view recognition in XA images of a heart. The XA image generation program may be extended to generate a dataset for disease recognition of the coronaries from an x-ray angiography (XA). The XA image generation program may be used to generate a dataset for the segmentation of a coronary artery tree by providing the XA image and the ground-truth labeling of the coronary artery.

According to at least one embodiment, the XA image generation program may start with generating at least one three-dimensional (3D) model of the heart and coronary arteries, either utilizing a curved surface or a captured point-cloud. During this stage, the XA image generation program may introduce randomness to remove coronary branches to simulate stenosis in part of an artery or the XA image generation program may apply affine transform to segments of the arteries to capture variations between different patients.

According to at least one embodiment, the XA image generation program may manually annotate and select different segments of the right coronary artery (RCA) and left coronary artery (LCA) branches. The annotation may also generate a skeletal model for the arteries. For each segment of the skeletal model, the XA image generation program may define a 3D axis that will be used to flip the coronary branch around the axis.

The present embodiment may include a 3D heart modeler. The 3D heart modeler (i.e., a tool developed to generate a heart model with variations of the coronary artery tree) may be utilized to generate a random coronary artery tree around a heart model, and the coronary artery tree may be generated procedurally or randomly configured by rotating or flipping existing coronary branches on a pre-saved model. The 3D heart modeler may be utilized to introduce a heart model that simulates one or more diseases affecting the coronaries. For example, a complete blockage may be modeled by removing coronary branches up to the leafs from the model, and stenosis may be introduced randomly by applying contractive transforms to none, or one or more coronary segments.

According to at least one embodiment, the XA image generation program may determine the primary and secondary angles of the camera and the x-ray source, and then may reproduce a projection of the model to produce a two-dimensional (2D) image view of the camera.

According to at least one embodiment, the XA image generation program may utilize a cycled generative adversarial (GAN) model to produce a realistic XA image from the 2D projection view.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a XA image generation program 110a. The networked computer environment 100 may also include a server 112 that is enabled to run a XA image generation program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 4, server computer 112 may include internal components 902a and external components 904a, respectively, and client computer 102 may include internal components 902b and external components 904b, respectively. Server computer 112 may also operate in a cloud computing service model, such as Software as a Service (SaaS), Analytics as a Service (AaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the XA image generation program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the XA image generation program 110a, 110b (respectively) to generate realistic XA images for deep learning consumption The XA image generation method is explained in more detail below with respect to FIGS. 2 and 3.

Figure 2:
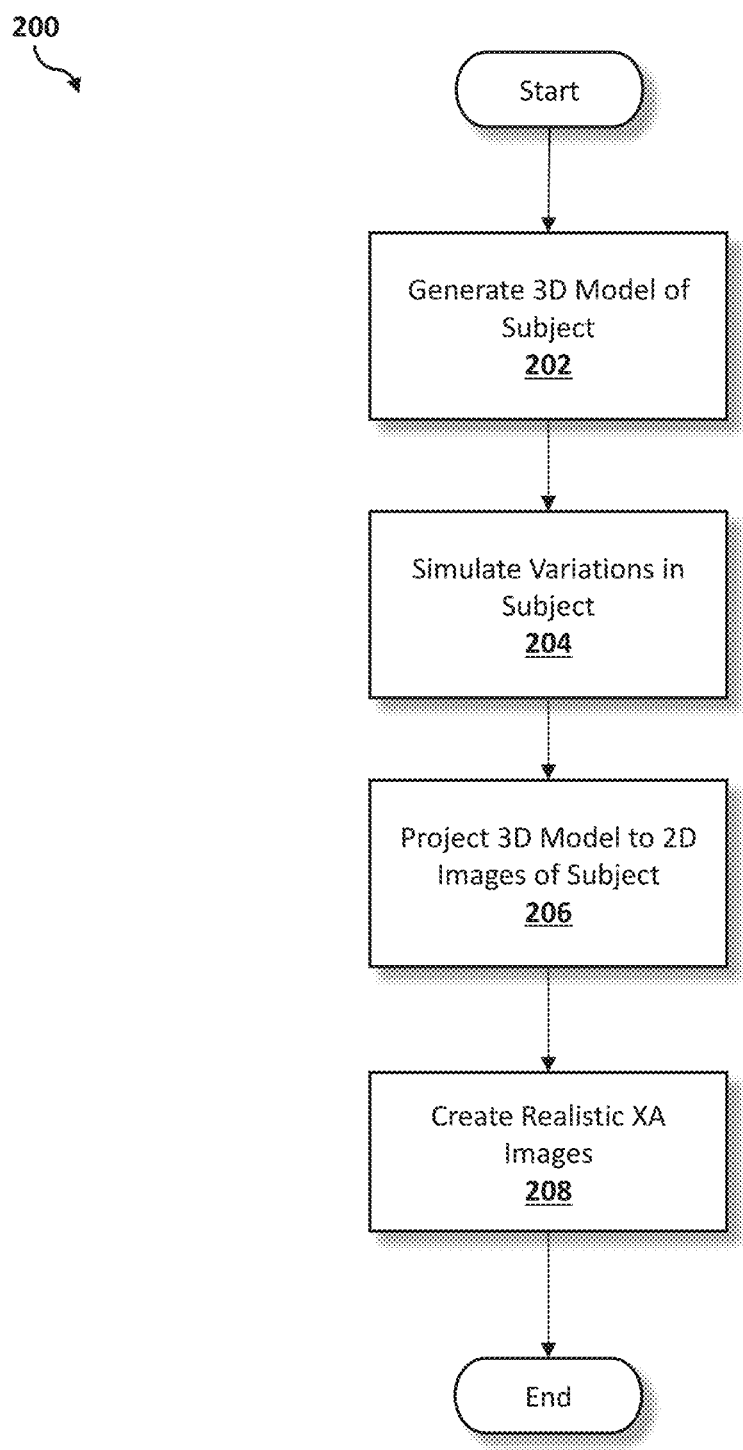
FIG. 2 is an operational flowchart illustrating a process for generating realistic x-ray angiography (XA) images according to at least one embodiment.

Referring now to FIG. 2, an operational flowchart illustrating the exemplary realistic XA image generation process 200 used by the XA image generation program 110a, 110b according to at least one embodiment is depicted.

At 202, a three-dimensional (3D) image of the subject is generated. The XA image generation program 110a, 110b may utilize an external generation engine to generate a heart model with variations to a coronary artery tree (i.e., 3D heart modeler). The 3D heart modeler may generate at least one random coronary artery tree associated with a model of the heart (i.e., subject).

Additionally, the 3D heart modeler may be utilized to introduce a heart model that simulates one or more diseases affecting the coronaries by introducing diseases to the coronaries. In the present embodiment, a complete blockage (i.e., total blockage) may be modeled by removing coronary branches up to the leafs of the 3D model. In another embodiment, the 3D heart modeler may randomly introduce stenosis, without blockage, (i.e., narrowing of the arteries) by applying contractive affine transforms to none, or one or more coronary segments. Specifically, the 3D heart modeler may randomly either select 0, 1 or more coronary branches and remove the branch up to the leaf to simulate a severe stenosis when the blood does not follow that branch, or by randomly selecting approximately 0 or more segments (e.g., LM or Left Main) the 3D heart modeler may define contractive affine transforms to simulate a mild coronary stenosis.

Based on the diseases introduced by the 3D heart modeler, the XA image generation program 110a, 110b may automatically create a disease profile for each disease introduced as a part of ground-truth labeling. As such, when the XA image generation program 110a, 110b detects that a new disease was introduced by the 3D heart modeler, the XA image generation program 110a, 110b may generate a disease profile. The disease profile may include the name of the introduced disease, the date and time that the disease was detected by the XA image generation program 110a, 110b, and 3D models associated with the disease. Once the disease profile is created, the user may be notified (e.g., via dialog box prompt) that a new disease profile has been created. The prompt may include the name of the disease profile and the location where the disease profile may be stored (e.g., database, cloud storage). The user may be able to change or modify the name of the disease profile and/or the location that the disease profile is stored. At the bottom of the dialog box, for example, there may be two buttons, "Yes, Modify" and "No, Continue". If the user clicks "Yes, Modify," the user may change the name of the disease profile and the location in which the disease profile will be stored. The user may be able to save the change to the location, and make that new location the default location for any future disease profiles. If, however, the user clicks "No, Continue," then the dialog box may disappear and the disease profile may be stored without modifications.

In another embodiment, the user may manually elect to delete a disease profile associated with a new disease introduced by the 3D heart modeler. When the user is notified that a new disease profile has been created, the user may click the "X" located at the top of the dialog box. The XA image generation program 110a, 110b may then open a second dialog box asking the user whether the user intends to not save the disease profile created by the 3D heart modeler. If the user clicks the "Yes" button located at the bottom of the dialog box, then the dialog box will disappear and the disease profile will not be saved. If, however, the user clicks the "No" button at the bottom of the dialog box, then the dialog box will disappear and the XA image generation program 110a, 110b will proceed with the process of saving the disease profile. The dialog box may also include a "More Details" button located at the bottom of the dialog box in which the user may view the information included within the disease profile before deciding whether the disease profile should be saved or not.

Generally, in a majority of instances, the 3D heart modeler may remove either the right coronary artery (RCA) or left coronary artery (LCA) to simulate the injected fluorescent dye. In one embodiment, the 3D heart modeler may include problematic examples (i.e., examples caused by common errors or omissions) in the dataset. A cardiologist, for example, makes a mistake and the dye is injected into both left and right branches during an angiography, and therefore, detection is made more difficult for the untrained eyes. The inclusion of such examples, with errors, may improve the accuracy of the 3D heart modeler during the training of the 3D heart modeler, since the 3D heart modeler may be able to identify issues in the dataset, create variations of the image with or without the errors, and utilize that image to generate a 3D model.

In one embodiment, the coronary artery tree may be randomly configured by rotating, perturbing or flipping segments (e.g., existing coronary branches on a pre-saved or pre-existing model) automatically. The pre-existing model (e.g., images of at least one coronary artery tree) may be retrieved from at least one external source (e.g., user, an application, at least one image stored in a database 114). The pre-existing model may be saved or stored on various media (e.g., hard drive, database 114, cloud storage). The pre-existing model may be retrieved based on a particular patient, demographic information (e.g., age, gender, ethnic group, weight) corresponding with the person associated with the pre-existing model, pre-existing condition(s) corresponding with the person associated with the pre-existing model, or a random selection process that depends on the user. Upon retrieval, the pre-existing model may be uploaded or fed into the XA image generation program 110a, 110b by using a software program 108 on the user's device (e.g., user's computer 102) that transmits the input pre-existing model via the communications network 116.

In another embodiment, the coronary artery tree may be generated by the 3D heart modeler procedurally, when there is no pre-existing model. The 3D heart modeler may utilize algorithms, including equations or geometrical formulas (e.g., curves and splines), to generate at least one coronary artery tree. The generated 3D model may be stored in a database 114, and the user may elect to add the generated 3D model as a pre-existing model for further access and use.

In an embodiment, the XA image generation program 110a, 110b may utilize at least one pre-existing model to simulate variations in the generated coronary artery tree. In another embodiment, the XA image generation program 110a, 110b may utilize multiple pre-existing models and randomly select one of the pre-existing models before applying the one or more variations to the generated coronary artery tree.

In the present embodiment, the XA image generation program 110a, 110b may save the configuration settings. For example, the user may select the "Settings" button located on the main screen of the XA image generation program 110a, 110b. After selecting the "Settings" button, the user may be prompted (e.g., via dialog box) to change or modify the configuration settings (e.g., the location in which the pre-existing models are retrieved from, the type of 3D models saved in the disease profiles, the segments of the 3D models, and additional default settings related to the generation of at least one 3D model in the XA image generation program 110a, 110b).

For example, a researcher should train a neural network to recognize the view from an XA image, namely cranial as opposed to caudal. As such, the researcher should gather a large dataset of real XA angiography images. However, due to the high expense and data privacy issues, the researcher does not have enough of these images to train the neural network. Therefore, the researcher utilizes the XA image generation program 110a, 110b to generate the necessary images to train the neural network. The researcher, who is working on a deep learning model to recognize the view in XA angiography images, first utilizes the 3D heart modeler to generate random 3D models of the LCA and RCA. The random 3D models are retrieved from a point cloud.

Next, at 204, variations of the subject are simulated. The XA image generation program 110a, 110b may determine the primary and secondary angles of the camera and the x-ray source of each 3D model. The XA image generation program 110a, 110b may also apply a randomly selected scale around 1.0 to each axis of the whole heart to simulate the heart going toward and away from the camera while breathing session or beating. The angles of the camera and the x-ray source of each 3D model may be saved as a part of the ground-truth labeling, and stored in a database (e.g., database 114). In another embodiment, the XA image generation program 110a, 110b may simulate one or more diseases associated with the subject.

Continuing the previous example, the researcher utilizes the XA image generation program 110a, 110b to simulate variations of the 3D models of the LCA and RCA from a patient. The simulations include the heart beating while the patient is breathing, exercising or stationary.

Then, at 206, at least one 3D model of the subject is projected to one or more two-dimensional (2D) images. For each variation of the subject, the XA image generation program 110a, 110b may project one or more 2D images of the heart from the at least one 3D model. The projected one or more 2D models (i.e., one or more 2D images) may be adjusted by changing the image quality (e.g., contrast, sharpness and brightness).

In one embodiment, when the 3D model is projected into one or more 2D images, the user is prompted (e.g., via dialog box) to change the image quality of the 2D images of the heart. The dialog box, for example, includes an interactive interface tool (e.g., slider, sliding radius bar) to alter or adjust the image quality of the 2D images in real-time. As such, as the user changes the image quality, the 2D images will change to reflect the changes to image quality applied by the user. Once the user is satisfied with the changes, then the user may click the "Change" button located at the bottom of the dialog box. If the user decides to not make any changes, the user may click the "Remain the Same" button located on the bottom of the dialog box. After clicking either the "Change" or "Remain the Same" button, the dialog box may disappear.

Continuing the previous example, the XA image generation program 110a, 110b generates multiple images of the RCA and LCA of the patient's heart to create several 2D models. The researcher is prompted to change the contrast, sharpness and brightness of each 2D image. Since the researcher decides not to make any adjustments to the contrast, sharpness and brightness, the researcher selects the "Remain the Same" button at the bottom of the dialog box. Therefore, there are no changes related to the contrast, sharpness or brightness of the 2D images.

Then, at 208, one or more realistic X-ray angiography (XA) images are created. The XA image generation program 110a, 110b may utilize a Cycle consistent GAN (i.e., a generative adversarial method or Cycle GAN model), which may mimic a distribution of data, to create one or more realistic XA images from the projected 2D image(s) of the synthetic coronary artery tree. The entire projected one or more 2D images or patches of the projected one or more 2D images may be utilized by the Cycle GAN model. The Cycle GAN model may then be utilized to train a deep convolutional neural network to map one or more synthetic images into one or more realistic XA images from the source domain to the target domain. The source domain (i.e., 2D images generated by the XA image generation program 110a, 110b) and target domain (i.e., images gathered by the user) may be stored on separate databases, or other external medium (e.g., records, separate files, disks or cloud storage).

To train (i.e., build) the deep convolutional neural network, the XA image generation program 110a, 110b may gather realistic XA images to represent the target domain. From the XA generation process 200, the XA image generation program 110a, 110b may gather the synthetic images to represent a source domain. The Cycle GAN model may then add the relevant background (e.g., ribs, catheter and marks) to each of the synthetic images.

In the present embodiment, the XA image generation program 110a, 110b may ignore, within reason, connectivity issues between different artery segments in the synthetic images. The Cycle GAN model may correct these connectivity issues (i.e., connectivity errors) and therefore, the XA image generation program 110a, 110b may not need to correct these connectivity issues to perfect the 3D model. For example, these connectivity errors may include two or more gaps between the cylinder segments that create a single coronary artery. Most of the coronary arteries may be generally smooth and curvy. If the XA image generation program 110a, 110b attempts to model these curves with multiple cylinders graphically and geometrically, then a small gap may appear between the cylinder segments, which may be ignored by the XA image generation program 110a, 110b.

Continuing the previous example, the XA image generation program 110a, 110b the utilizes the Cycle GAN model to create 122 realistic XA images from the simulated variations of the 2D images. The 2D images generated by XA image generation program 110a, 110b become a source domain. In addition, the researcher gathers 98 realistic XA images from the researcher's own sources associated with the target domain. The researcher utilizes these images from the target and source domains to train the final deep convolutional neural network model to determine the view from the XA angiography images. After the Cycle GAN model is utilized to train the deep convolutional neural network to map synthetic images to realistic images, the researcher has over 2,500 realistic images that may be used for the further training of the deep convolutional neural network, or for the researcher's own model.

In another embodiment, the XA image generation program 110a, 110b may be extended to various organs (e.g., kidney, lungs) associated with a living organism (e.g., humans or animals).

Figure 3:
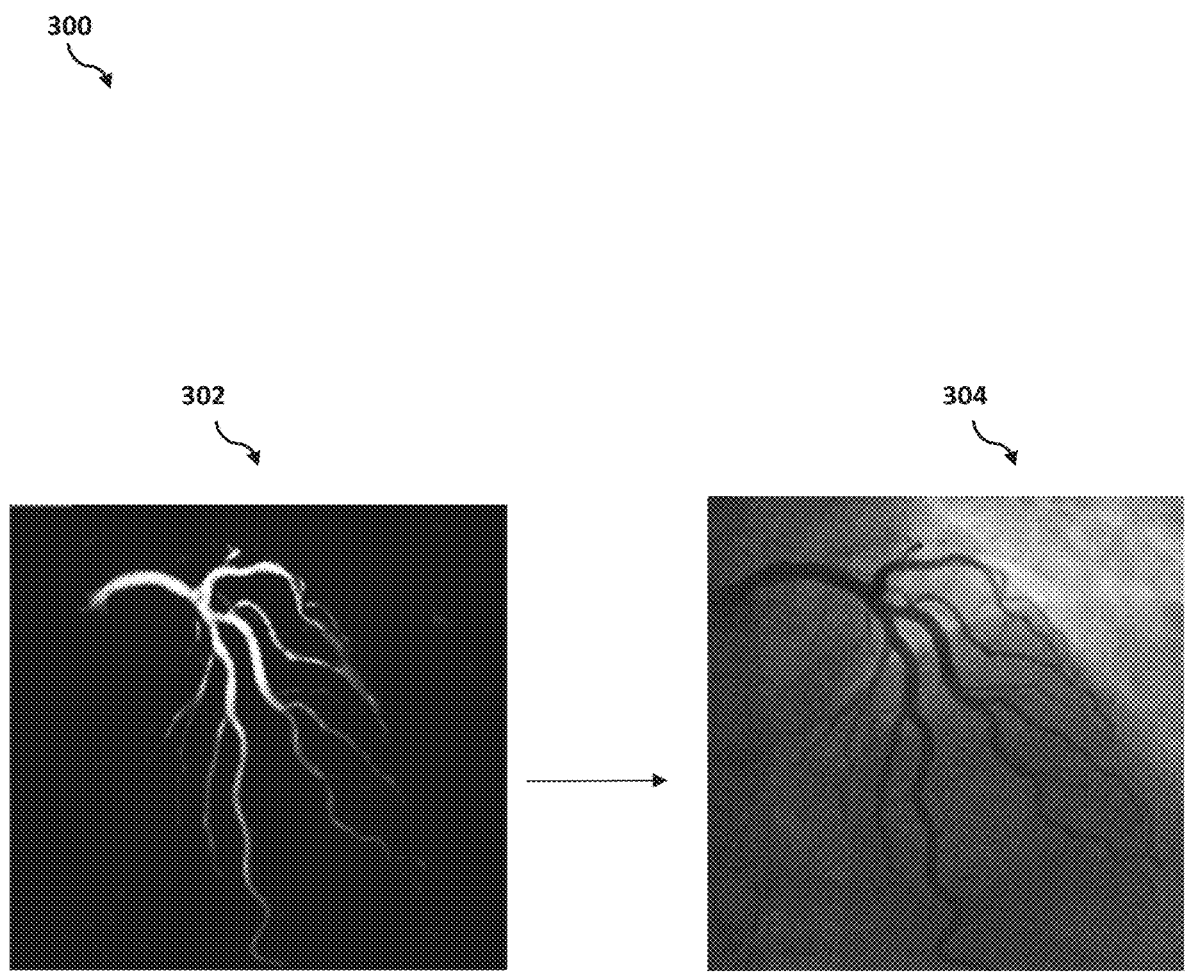
FIG. 3 is a comparison of x-ray angiography (XA) images between a XA image of a synthetic coronary artery tree and a realistic XA image of a coronary artery tree according to at least one embodiment.

Referring now to FIG. 3, a comparison of the XA images between a synthetic XA image of the coronary artery tree and a realistic XA image of the coronary artery tree in accordance with one embodiment is depicted. A synthetic XA image of coronary artery tree 302 that may be retrieved by a source domain from the user or the XA image generation program 110a, 110b is shown. The XA image generation program 110a, 110b may then utilize the Cycle GAN model to add the relevant background and resolve any connectivity errors to the synthetic image 302. A trained deep convolutional neural network may then be utilized to map the synthetic images and generate a realistic XA image of the same coronary artery tree 304.

The functionality of a computer may be improved by the XA image generation program 110a, 110b because the XA image generation program 110a, 110b may utilize a deep convolutional neural network to generate realistic XA images in the field of medical image computing. Such realistic XA images may be used in research and patient treatment, as well as teaching the angiography procedure to prospective students. The XA image generation program 110a, 110b presents more improvements on the existing capabilities and functionalities of the computer and the usability of XA images in research, education and patient treatment since acquiring real XA images is expensive and requires a patient to be exposed to multiple x-ray sources, thereby the XA image generation program 110a, 110b generates XA images that can help with the training of the machine learning systems that help with diagnosis and treatment of heart diseases.

It may be appreciated that FIGS. 2 and 3 provide only an illustration of one embodiment and do not imply any limitations with regard to how different embodiments may be implemented. Many modifications to the depicted embodiment(s) may be made based on design and implementation requirements.

Figure 4:
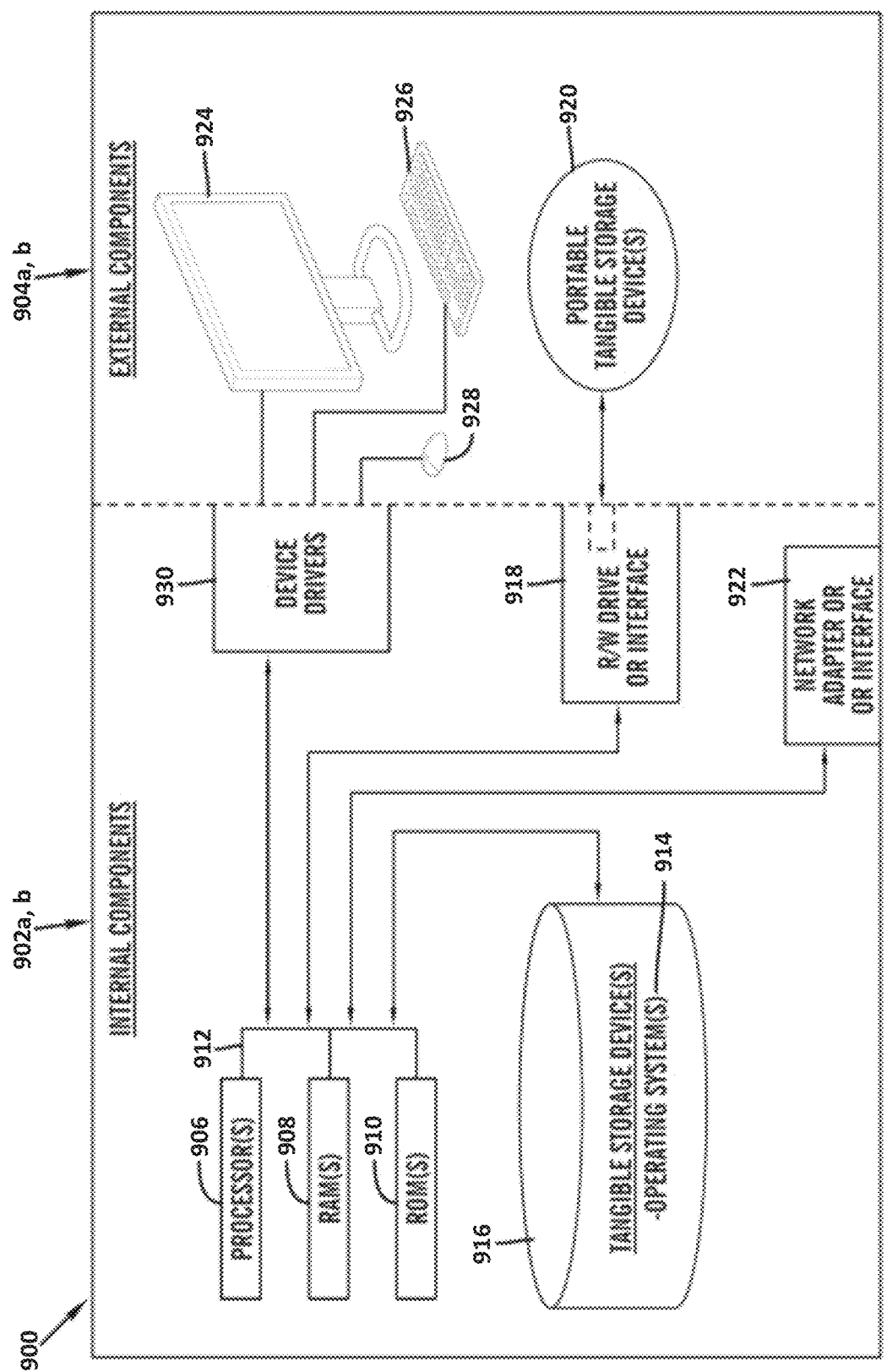
FIG. 4 is a block diagram of internal and external components of computers and servers depicted in FIG. 1 according to at least one embodiment.

FIG. 4 is a block diagram 900 of internal and external components of computers depicted in FIG. 1 in accordance with an illustrative embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 a, b and external components 904 a, b illustrated in FIG. 4. Each of the sets of internal components 902 a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108 and the XA image generation program 110a in client computer 102, and the XA image generation program 110b in network server 112, may be stored on one or more computer-readable tangible storage devices 916 for execution by one or more processors 906 via one or more RAMs 908 (which typically include cache memory). In the embodiment illustrated in FIG. 4, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the XA image generation program 110a, 110b can be stored on one or more of the respective portable computer-readable tangible storage devices 920, read via the respective R/W drive or interface 918 and loaded into the respective hard drive 916.

Each set of internal components 902 a, b may also include network adapters (or switch port cards) or interfaces 922 such as a TCP/IP adapter cards, wireless Wi-Fi interface cards, or 3G or 4G wireless interface cards or other wired or wireless communication links. The software program 108 and the XA image generation program 110a in client computer 102 and the XA image generation program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the XA image generation program 110a in client computer 102 and the XA image generation program 110b in network server computer 112 are loaded into the respective hard drive 916. The network may comprise copper wires, optical fibers, wireless transmission, routers, firewalls, switches, gateway computers and/or edge servers.

Each of the sets of external components 904 a, b can include a computer display monitor 924, a keyboard 926, and a computer mouse 928. External components 904 a, b can also include touch screens, virtual keyboards, touch pads, pointing devices, and other human interface devices. Each of the sets of internal components 902 a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Analytics as a Service (AaaS): the capability provided to the consumer is to use web-based or cloud-based networks (i.e., infrastructure) to access an analytics platform. Analytics platforms may include access to analytics software resources or may include access to relevant databases, corpora, servers, operating systems or storage. The consumer does not manage or control the underlying web-based or cloud-based infrastructure including databases, corpora, servers, operating systems or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
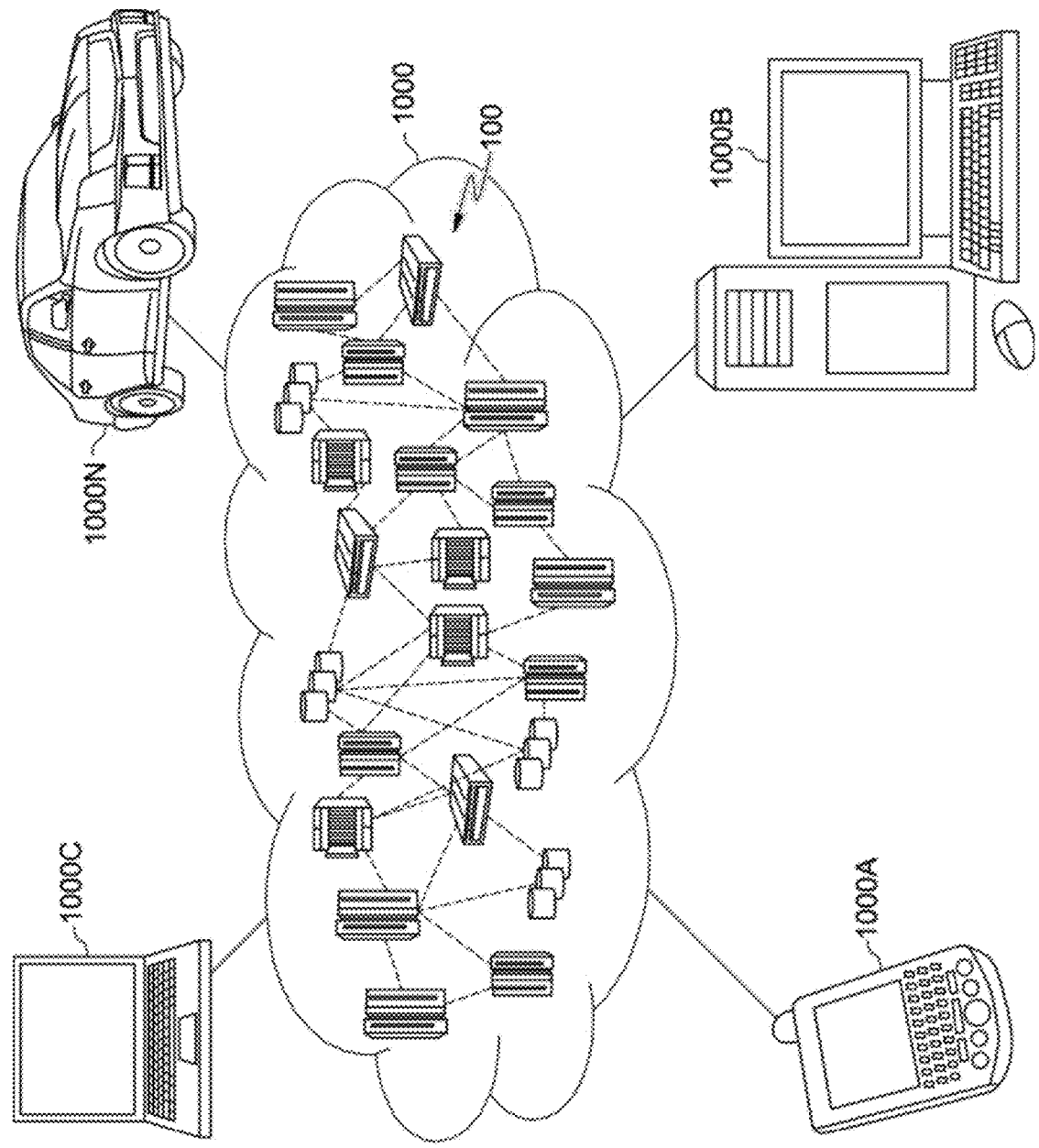
FIG. 5 is a block diagram of an illustrative cloud computing environment including the computer system depicted in FIG. 1, in accordance with an embodiment of the present disclosure.

Referring now to FIG. 5, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 5 are intended to be illustrative only and that computing nodes 100 and cloud computing environment 1000 can communicate with any type of computerized device over any type of network and/or network addressable connection (e.g., using a web browser).

Figure 6:
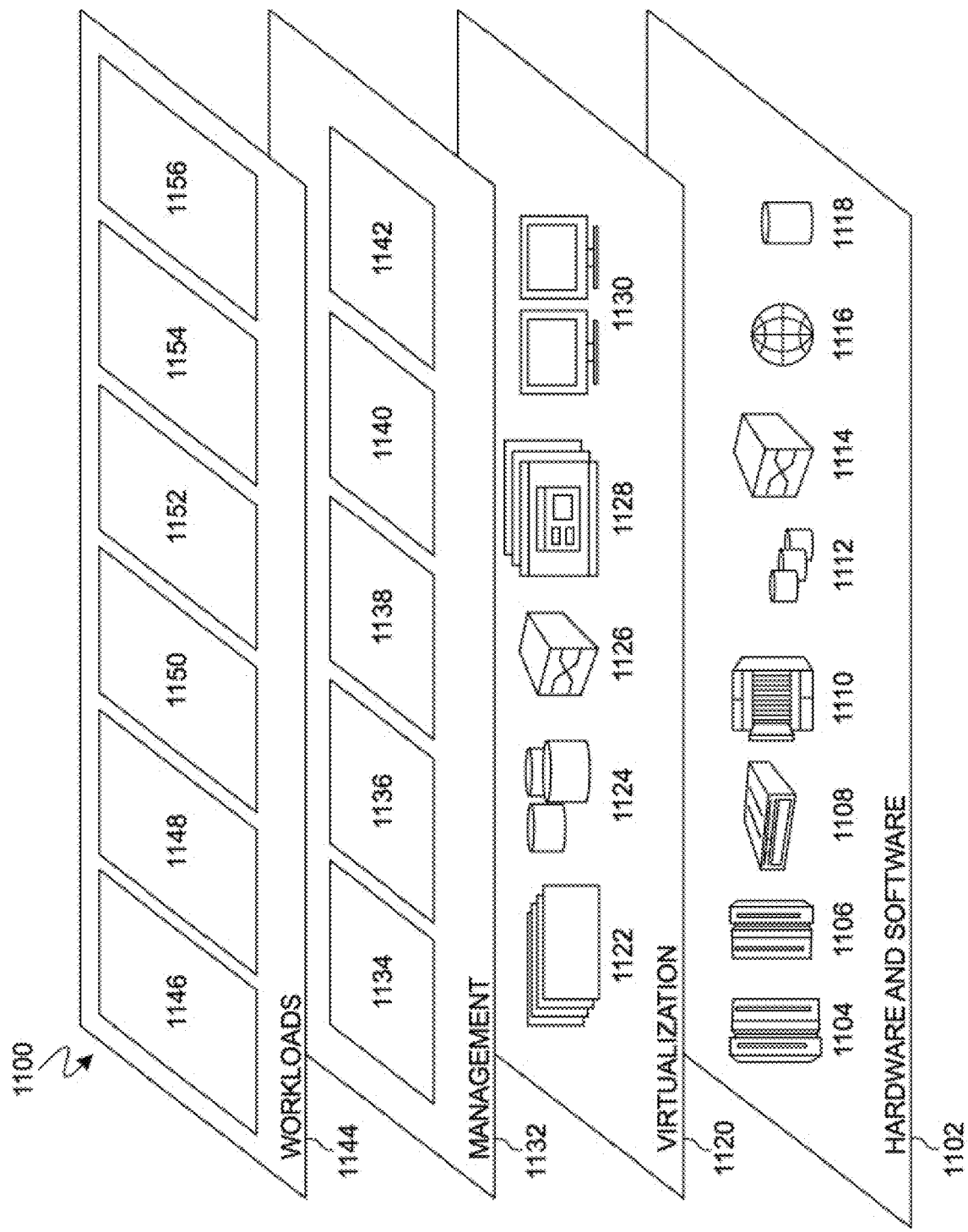
FIG. 6 is a block diagram of functional layers of the illustrative cloud computing environment of FIG. 5, in accordance with an embodiment of the present disclosure.

Referring now to FIG. 6, a set of functional abstraction layers 1100 provided by cloud computing environment 1000 is shown. It should be understood in advance that the components, layers, and functions shown in FIG. 6 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and XA image generation 1156. A XA image generation program 110a, 110b provides a way to generate at least one XA image for deep learning consumption.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for generating one or more realistic x-ray angiography (XA) images for deep learning, the method comprising:
    generating two or more three-dimensional (3D) models associated with a subject, each of the models simulating a variation to an artery tree;
    projecting each of the generated two or more 3D models associated with the subject into one or more two-dimensional (2D) images associated with the subject;
    creating the one or more realistic XA images of the subject from the one or more 2D images associated with the subject by utilizing a trained deep convolutional neural network;
    detecting, by a three-dimensional (3D) heart modeler, at least one disease associated with the subject; and
    creating, automatically, a disease profile for the detected at least one disease associated with the subject.

2. The method of claim 1, wherein each of the two or more simulated variations to an artery tree corresponds with a camera and an x-ray, and wherein one or more angles of the subject are stored in a database as a part of the ground-truth labeling.

3. The method of claim 1 in which the subject includes an organ associated with a living organism.

4. The method of claim 2, further comprising:
    analyzing the two or more simulated variations to an artery tree;
    generating the one or more 2D images associated with the subject for each of the analyzed two or more simulated variations to an artery tree; and
    modifying a plurality of image quality settings associated with the generated one or more 2D images.

5. The method of claim 1, wherein generating two or more three-dimensional (3D) models associated with a subject, each of the models simulating a variation to an artery tree, further comprises:
    retrieving, automatically, at least one pre-existing model associated with the subject from an external source; and
    transmitting the retrieved at least one pre-existing model associated with the subject to a computing device.

6. The method of claim 1, further comprising:
    gathering the generated one or more 2D images associated with a target domain and one or more synthetic images associated with a source domain;
    adding, by utilizing a Cycle GAN model, at least one form of relevant background to each of the one or more synthetic images; and
    building the trained deep convolutional neural network to map one or more synthetic images from the source domain into one or more realistic XA images from the target domain.

7. A computer system for generating one or more realistic x-ray angiography (XA) images for deep learning, comprising:
    one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
    generating two or more three-dimensional (3D) models associated with a subject, each of the models simulating a variation to an artery tree;
    projecting each of the generated two or more 3D models associated with the subject into one or more two-dimensional (2D) images associated with the subject;
    creating the one or more realistic XA images of the subject from the one or more 2D images associated with the subject by utilizing a trained deep convolutional neural network;
    detecting, by a three-dimensional (3D) heart modeler, at least one disease associated with the subject; and
    creating, automatically, a disease profile for the detected at least one disease associated with the subject.

8. The computer system of claim 7, wherein each of the two or more simulated variations to an artery tree corresponds with a camera and an x-ray, and wherein one or more angles of the subject are stored in a database as a part of the ground-truth labeling.

9. The computer system of claim 7 in which the subject includes an organ associated with a living organism.

10. The computer system of claim 8, further comprising:
    analyzing the two or more simulated variations to an artery tree;
    generating the one or more 2D images associated with the subject for each of the analyzed two or more simulated variations to an artery tree; and
    modifying a plurality of image quality settings associated with the generated one or more 2D images.

11. The computer system of claim 7, wherein generating two or more three-dimensional (3D) models associated with a subject, each of the models simulating a variation to an artery tree, further comprises:
    retrieving, automatically, at least one pre-existing model associated with the subject from an external source; and
    transmitting the retrieved at least one pre-existing model associated with the subject to a computing device.

12. The computer system of claim 7, further comprising:
    gathering the generated one or more 2D images associated with a target domain and one or more synthetic images associated with a source domain;
    adding, by utilizing a Cycle GAN model, at least one form of relevant background to each of the one or more synthetic images; and
    building the trained deep convolutional neural network to map one or more synthetic images from the source domain into one or more realistic XA images from the target domain.

13. A computer program product for generating one or more realistic x-ray angiography (XA) images for deep learning, comprising:
    one or more computer-readable storage media and program instructions stored on at least one of the one or more tangible storage media, the program instructions executable by a processor to cause the processor to perform a method comprising:
    generating two or more three-dimensional (3D) models associated with a subject, each of the models simulating a variation to an artery tree;

projecting each of the generated two or more 3D models associated with the subject into one or more two-dimensional (2D) images associated with the subject;

creating the one or more realistic XA images of the subject from the one or more 2D images associated with the subject by utilizing a trained deep convolutional neural network;

detecting, by a three-dimensional (3D) heart modeler, at least one disease associated with the subject; and creating, automatically, a disease profile for the detected at least one disease associated with the subject.

14. The computer program product of claim 13, wherein each of the two or more simulated variations to an artery tree corresponds with a camera and an x-ray, and wherein one or more angles of the subject are stored in a database as a part of the ground-truth labeling.

15. The computer program product of claim 13 in which the subject includes an organ associated with a living organism.

16. The computer program product of claim 14, further comprising:

analyzing the two or more simulated variations to an artery tree;

generating the one or more 2D images associated with the subject for each of the analyzed two or more simulated variations to an artery tree; and modifying a plurality of image quality settings associated with the generated one or more 2D images.

17. The computer program product of claim 13, wherein generating two or more three-dimensional (3D) models associated with a subject, each of the models simulating a variation to an artery tree, further comprises:

retrieving, automatically, at least one pre-existing model associated with the subject from an external source; and transmitting the retrieved at least one pre-existing model associated with the subject to a computing device.

18. The computer program product of claim 13, further comprising:

gathering the generated one or more 2D images associated with a target domain and one or more synthetic images associated with a source domain;

adding, by utilizing a Cycle GAN model, at least one form of relevant background to each of the one or more synthetic images; and building the trained deep convolutional neural network to map one or more synthetic images from the source domain into one or more realistic XA images from the target domain.

* * * * *